(12) United States Patent
Marlow et al.

(10) Patent No.: US 10,368,784 B2
(45) Date of Patent: Aug. 6, 2019

(54) SENSOR DATA DAMPING

(71) Applicant: Microsoft Technology Licensing, LLC, Redmond, WA (US)

(72) Inventors: Christopher Richard Marlow, Hinckley (GB); Eike Jens Umlauf, Tamworth (GB); Andrew John Preston, Market Bosworth (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 754 days.

(21) Appl. No.: 14/311,878

(22) Filed: Jun. 23, 2014

(65) Prior Publication Data

US 2015/0369864 A1 Dec. 24, 2015

(51) Int. Cl.
*G01R 31/317* (2006.01)
*A61B 5/11* (2006.01)
*G06F 3/01* (2006.01)
*G06F 3/03* (2006.01)

(52) U.S. Cl.
CPC ............ *A61B 5/1128* (2013.01); *G06F 3/011* (2013.01); *G06F 3/0304* (2013.01)

(58) Field of Classification Search
CPC .. G01R 31/31709; A61B 5/1128; G06F 3/041
USPC ........................................................ 702/191
See application file for complete search history.

(56) References Cited

U.S. PATENT DOCUMENTS

| 5,638,092 | A | 6/1997 | Eng et al. |
| 6,411,744 | B1 | 6/2002 | Edwards |
| 7,227,526 | B2 | 6/2007 | Hildreth et al. |
| 7,292,151 | B2 | 11/2007 | Ferguson et al. |
| 7,474,772 | B2 | 1/2009 | Russo et al. |
| 8,384,714 | B2 | 2/2013 | De Aguiar et al. |
| 2009/0149257 | A1* | 6/2009 | Ferguson ............ A61B 5/1124 463/37 |
| 2009/0192619 | A1 | 7/2009 | Martin et al. |
| 2010/0249867 | A1* | 9/2010 | Wanasek ............ A61B 5/0428 607/28 |
| 2010/0281432 | A1* | 11/2010 | Geisner ................. G06F 3/011 715/849 |

(Continued)

OTHER PUBLICATIONS

Schonauer, et al., "Full Body Interaction for Serious Games in Motor Rehabilitation", In Proceedings of the 2nd Augmented Human International Conference, Mar. 12, 2011, 8 pages.

(Continued)

*Primary Examiner* — Yoshihisa Ishizuka
(74) *Attorney, Agent, or Firm* — Klarquist Sparkman, LLP

(57) ABSTRACT

Sensor data damping is described, for example, to remove jitter from sensor data to enable control of a computing device. In various examples damped sensor data is compared with a threshold and clamped to the threshold in the case a difference between the sensor data and the damped sensor data is above the threshold. In various examples the damped data has low-latency and is used to control a downstream system such as a game system, natural user interface, robotic system, augmented reality system or other system. In examples, the threshold is adjusted on the fly on the basis of any one or more of: state data from the downstream system, frequency of clamping, velocity of the sensor data. In some examples, the sensor data comprises human/animal joint positions from a depth sensor.

20 Claims, 12 Drawing Sheets

(56) References Cited

U.S. PATENT DOCUMENTS

| | | | | |
|---|---|---|---|---|
| 2011/0262002 | A1* | 10/2011 | Lee | G06F 3/017 |
| | | | | 382/103 |
| 2013/0027293 | A1* | 1/2013 | Baele | G06F 3/011 |
| | | | | 345/156 |
| 2013/0181908 | A1 | 7/2013 | Santiago et al. | |
| 2013/0265242 | A1* | 10/2013 | Richards | G06F 3/0418 |
| | | | | 345/173 |
| 2014/0239602 | A1* | 8/2014 | Blankenship | B60G 17/0152 |
| | | | | 280/5.515 |

OTHER PUBLICATIONS

Langdon, et al., "Statistical Estimation of User's Intentions from Motion Impaired Cursor use Data", In Proceeding of 6th International Conference Series on Disability, Virtual Reality and Associated Technologies, Sep. 18, 2006, pp. 141-146.

Kjeldsen, et al., "Toward the Use of Gesture in Traditional User Interfaces", In Proceedings of the Second International Conference on Automatic Face and Gesture Recognition, Oct. 14, 1996, pp. 151-156.

MathHelper.Clamp Method, "XNA Game Studio 3.1," Jan. 11, 2010, retrieved form Internet Archive Wayback Machine from <<http:///web.archive.org/web/20100111230725/http://msdn.microsoft.com/en-us/library/micr . . . >> on Mar. 28, 2017.

* cited by examiner

SENSOR DATA DAMPING

Sensor data, such as motion tracking sensor data, audio sensor data, temperature sensor data, light sensor data, and other environmental sensor data is typically noisy due to noise in the sensor equipment and/or noise introduced during measurement processes. The noise in the sensor data makes it difficult to accurately control downstream systems using the sensor data. For example, to control a robot, natural user interface, voice activated recording system or other system.

One approach to ameliorating noise in sensor data is to dampen the data. Where noise results in jitter, or oscillations in a sensor data signal, damping may be used to reduce or restrict the jitter. Different types of damping mechanisms are known such as springs, viscous drag in mechanical systems, resistance in electronic oscillators and absorption and scattering of light in optical oscillators.

Where sensor data is damped in direct proportion to an instantaneous rate of change of the sensor data, the damping is referred to as linear damping. Linear damping processes such as those using a restoring force (such as due to a spring) that is proportional to the change in the sensor signal, and in the opposite direction, are often used.

The embodiments described below are not limited to implementations which solve any or all of the disadvantages of known sensor data damping systems.

SUMMARY

The following presents a simplified summary of the disclosure in order to provide a basic understanding to the reader. This summary is not an extensive overview of the disclosure and it does not identify key/critical elements or delineate the scope of the specification. Its sole purpose is to present a selection of concepts disclosed herein in a simplified form as a prelude to the more detailed description that is presented later.

Sensor data damping is described, for example, to remove jitter from sensor data to enable control of a computing device. In various examples damped sensor data is compared with a threshold and clamped to the threshold in the case a difference between the sensor data and the damped sensor data is above the threshold. In various examples the damped data has low-latency and is used to control a downstream system such as a game system, natural user interface, robotic system, augmented reality system or other system. In examples, the threshold is adjusted on the fly on the basis of any one or more of: state data from the downstream system, frequency of clamping, velocity of the sensor data. In some examples, the sensor data comprises human/animal joint positions from a depth sensor.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Although the present examples are described and illustrated herein as being implemented in a joint position tracking system controlling a game system or natural user interface (NUI), the system described is provided as an example and not a limitation. As those skilled in the art will appreciate, the present examples are suitable for application in a variety of different types of control systems using sensor data.

Figure 1:
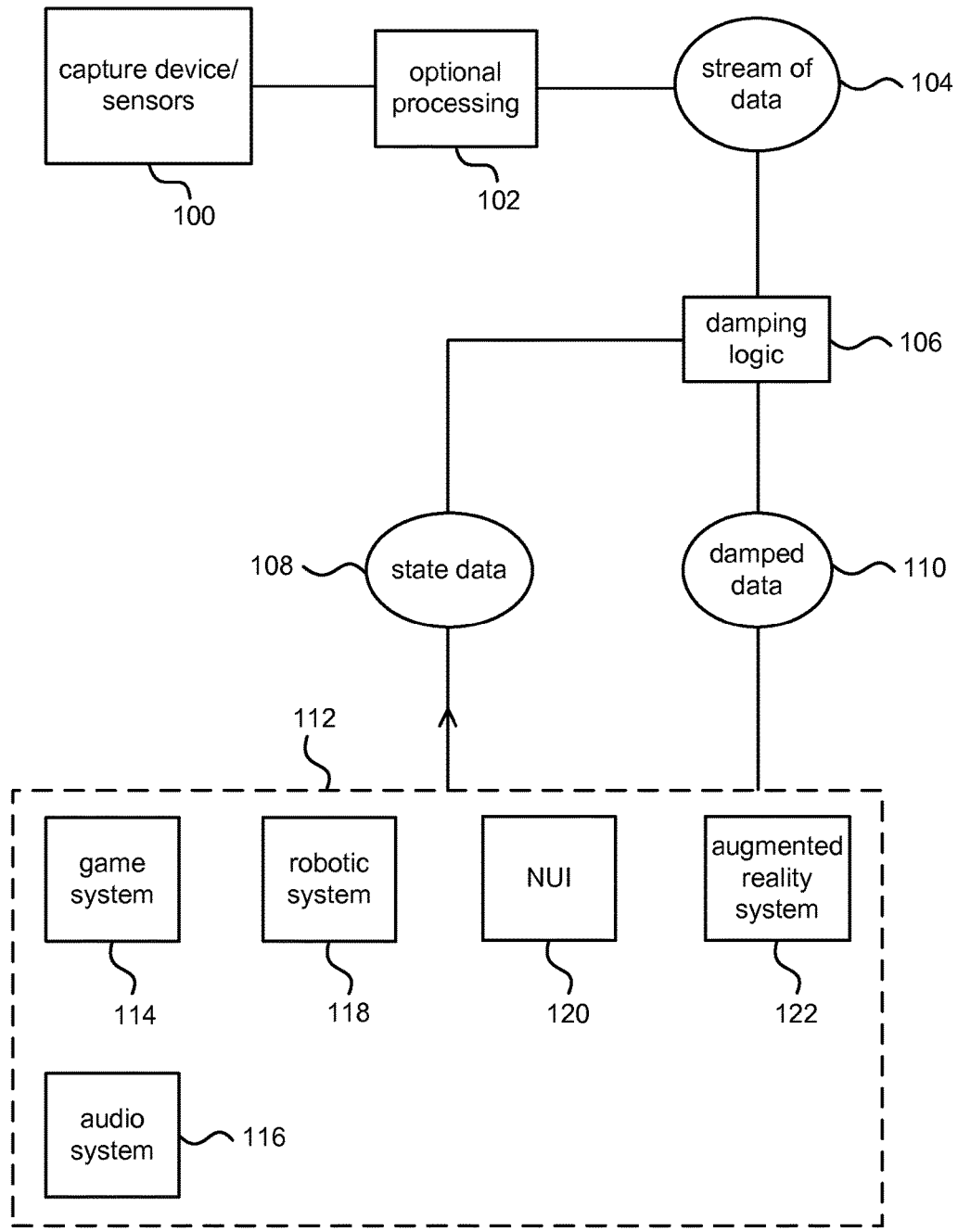
FIG. 1 is a schematic diagram of a damping system deployed to damp a stream of data from a capture device.

FIG. 1 is a schematic diagram of a damping logic 106 deployed to damp a stream of data 104 from a capture device 100. The damping logic receives the stream of data 104 either in a raw form or where the sensor data has been processed (using optional processing module 102) to derive features, or characteristics of the sensor data which are computed in advance of damping.

The sensor data is captured by one or more capture devices/sensors 100. A non-exhaustive list of examples of capture devices/sensors is: depth camera, color camera, microphone, light sensor, thermometer, pressure sensor, orientation sensor, position sensor.

The optional processing module 102 computes features or characteristics of the sensor data. For example, where the sensor data comprises depth images captured by one or more cameras the optional processing module may compute joint positions of articulated entities in the field of view of the depth camera. Articulated entities are jointed entities such as humans, animals, robots, or parts such as hands. In another example, the sensor data comprises depth images and the optional processing module computes body part centroids. In another example, the sensor data comprises microphone output from a plurality of microphones in a room and the optional processing module computes locations of people in the room who are speaking. In another example, the sensor data comprises pressure sensor data from a surface of a device and the optional processing module computes locations of one or more objects touching the surface. In another example, the sensor data comprises orientation sensor data from a tablet computer or other computing device and the processing module computes orientation of the device.

The stream of data 104 is input to the damping logic 106. For example, where the capture device 100 is a camera such as a video camera, the stream of data 104 is input at a frame rate of the camera to the damping logic 106. The damping logic is computer-implemented using software and/or hardware. The damping logic 106 outputs damped data 110 to a downstream computing system 112 to enable control of the downstream computing system. Examples of downstream computing systems 112 include but are not limited to: a game system 114, a robotic system 118, a natural user interface (NUI) 120, an augmented reality system 122, an audio system 116. The downstream computing system may output state data 108 and make that state data available to the damping logic 106. For example, the damping logic may query an application programming interface of the downstream system 112 and/or an operating system of the downstream computing system 112. The state data 108 may be actively sent by the downstream computing system to the damping logic 106 in some examples. The state data 108 comprises information about current operation of the downstream computing system at a given point in time. For example, the state data 108 may comprise values of parameters, entries in buffers, flag settings and other data indicating a current point of operation reached by the downstream system. For example, in the case of a game system 114 the state data may comprise information about a situation in a game that has been reached.

The damping logic 106 processes the stream of data 104 to damp that data so as to counteract noise in the stream of data 104. The damping logic uses a clamping mechanism to remove latency from the damped data 110. The clamping mechanism comprises using a threshold (which may be changed on the fly) and is described in more detail below with reference to FIG. 8. Latency in this context is a lag between a damped version of a data stream and the corresponding raw data stream. In the example of FIG. 1 the raw data stream is the stream of data 104 and the damped version of the data stream is the damped data 110. When lag occurs the control of the downstream system 112 is impaired. Lag is especially severe where large magnitude changes in the sensed data occur over a short time scale. This type of situation arises often where the sensed data is used to track position of a moving entity. For example, joint positions of players of a natural user interface game, touch positions of a user on a pressure sensitive surface, orientation positions of a movable computing device. Many other application domains involve tracking large magnitude changes in sensed data that occur over a short time scale. The examples given here are not intended to be limiting.

Figure 2:
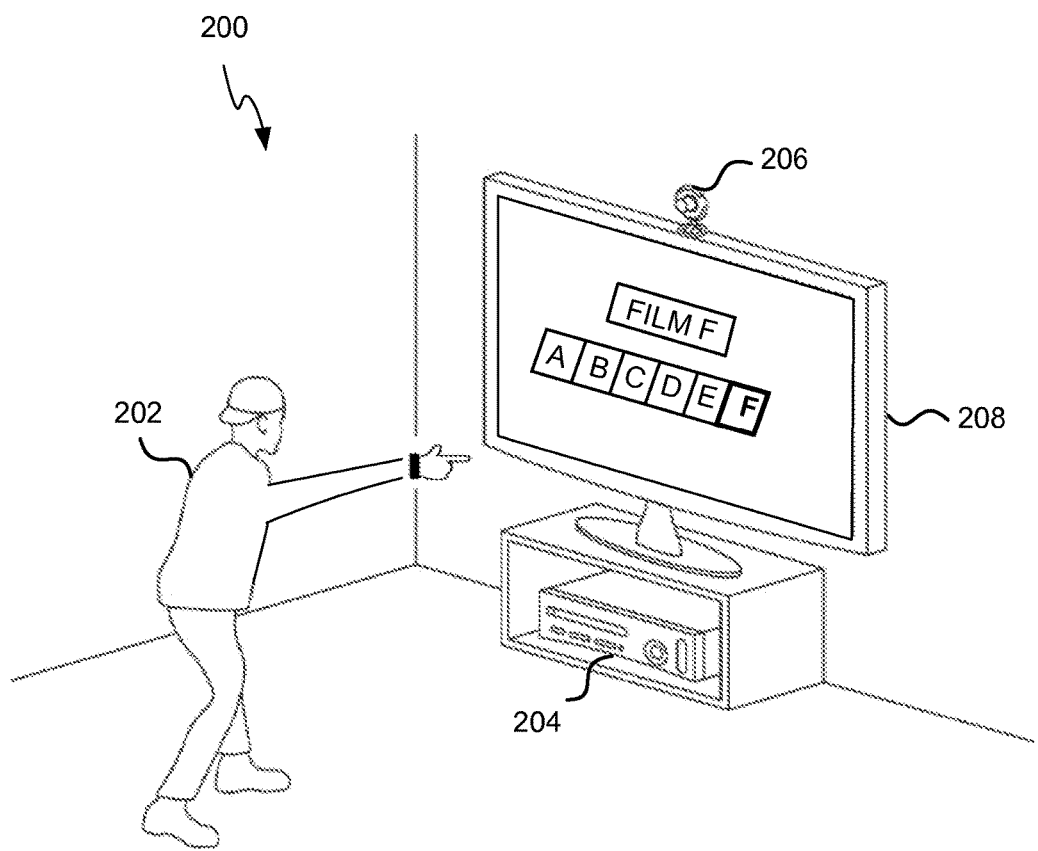
FIG. 2 illustrates an example camera-based control system for controlling a natural user interface.

FIG. 2 illustrates an example camera-based control system 200 for controlling a natural user interface. FIG. 2 shows a user 202 pointing at, in this illustrative example, a graphical user interface for text input, whereby the user 202 is able to point at letters of the alphabet in order to input text to a search query box. The, camera-based control system 200 can be used to, among other things, detect pointing location of the user 202 and control the user interface on the basis of the detected point location.

The camera-based control system 200 comprises a computing device 204. The computing device 104 can be a general purpose computer, gaming system or console, or dedicated image processing device. The computing device 204 can include hardware components and/or software components such that the computing device 204 can be used to execute applications such as gaming applications and/or non-gaming applications. The structure of the computing device 204 is discussed hereinafter with reference to FIG. 12.

The camera-based control system 200 further comprises a capture device 206. The capture device 106 can be, for example, an image sensor or detector that can be used to visually monitor one or more users (such user 202) such that gestures performed by the one or more users can be captured, analyzed, processed, and tracked to perform one or more controls or actions within a game or application, as described in more detail below.

The camera-based control system 200 can further comprise a display device 208 connected to the computing device 204. The computing device can be a television, a monitor, a high-definition television (HDTV), or the like that can provide game or application visuals (and optionally audio) to the user 202.

In operation, the user 202 can be tracked using the capture device 206 such that the joint positions, movements and size of user 202 can be interpreted by the computing device 204 (and/or the capture device 206) as controls that can be used to affect the application being executed by computing device 204. As a result, the user 202 can move his or her body to control a natural user interface.

Movement of the user 202 can be used and analyzed in any suitable manner to interact with applications the natural user interface, for example to enter text, select icons or menu items, control media playback, browse websites or operate any other controllable aspect of an operating system or application.

A damping logic (such as damping logic 106 of FIG. 1) is located at the computing device 204 or the capture device 206. In some examples, the damping logic is distributed between the computing device 204 and the capture device 206. The damping logic acts to remove noise from data captured by the capture device in such a way that lag or latency between the raw captured data and the damped data is reduced.

For example, where the user 202 points at the display to select letters of the alphabet (such as in FIG. 2) the user typically tries to point at the same screen location for period of time. The pointing location of the user 202, calculated from the captured images (captured by capture device 206) is noisy due to both noise introduced by the capture device 206 and also due to movement of the user's arm.

A damping logic may be used to remove at least part of this noise as described in more detail below. The damping logic may use a threshold and may clamp damped values to the threshold in some situations. The threshold may be adapted dynamically.

When the user makes a large movement over a relatively short time, for example, to point at a graphical element on one side of the display and then point at a graphical element on another side of the display, the damping system avoids latency or lag between the sensed pointing location and the damped version of the sensed pointing location. This is particularly useful for control of the natural user interface because any lag in the damped data results in a corresponding, or exacerbated, lag in the natural user interface display.

Figure 3:
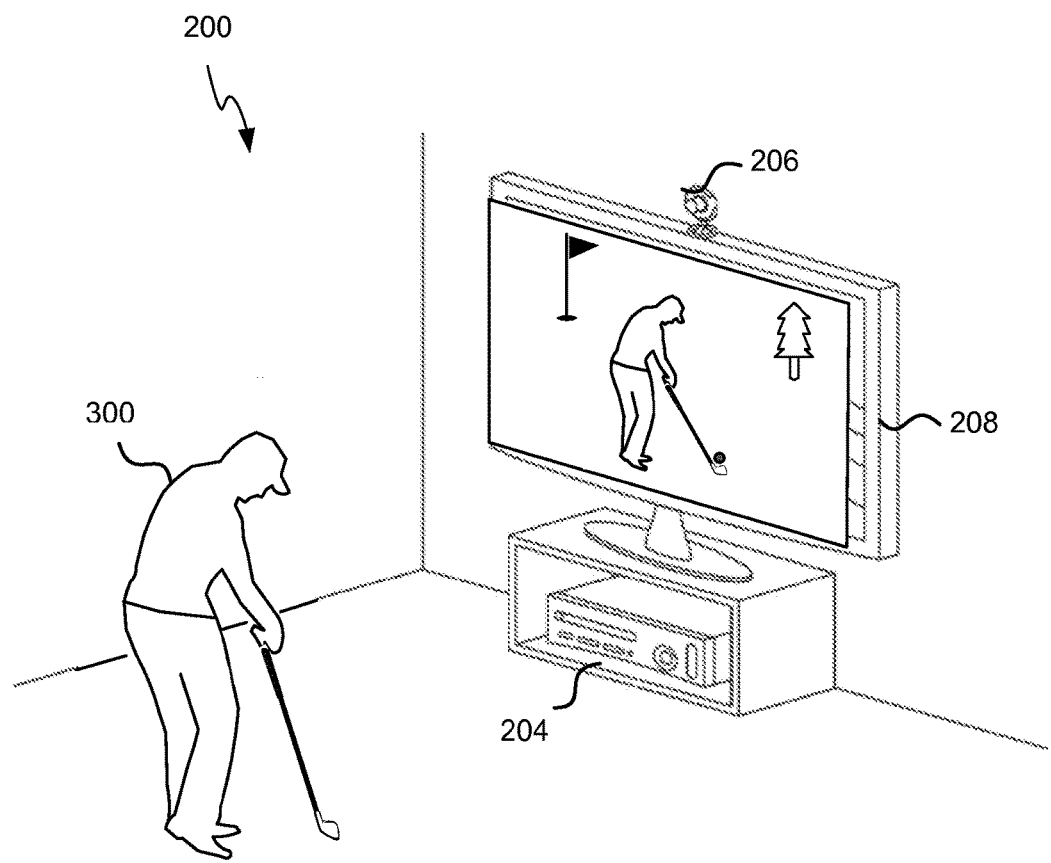
FIG. 3 illustrates an example camera-based control system for controlling a computer game.

FIG. 3 illustrates an example camera-based control system for controlling a computer game. The camera-based control system 200 is the same as that of FIG. 2 except that the application executing on the computing device 204 is a golf game that the user 202 is playing. In this example, the computing device 204 controls the display device 208 to provide a visual representation of the user 202 as a golfer playing avatar on a golf course. The computing device 204 controls the display device 208 to provide a visual representation of an avatar that the user 202 can control with his or her movements. For example, the user 202 can make a golf swing (using a real golf club but no golf ball) to cause the user avatar to hit a golf ball in game space. Thus, according to this example, the computing device 204 and the capture device 206 of the camera-based control system 200 can be used to recognize and analyze the golf swing of the user 202 in physical space such that the golf swing may be interpreted as a game control of the user avatar in game space.

Whilst the user 202 is holding the golf club noise in the captured images captured by the capture device 206 occurs. The noise may be due to noise resulting from the camera and/or from movement of the user 202. A damping logic located at the computing device 204 and/or the capture device 206 is used as in the example described with reference to FIG. 2. The damping logic acts to remove noise from data captured by the capture device in such a way that lag or latency between the raw captured data and the damped data is reduced.

When the user makes a large movement over a relatively short time, for example, during a golf swing, the damping logic avoids latency or lag between the sensed joint positions and a damped version of the sensed joint positions. This is particularly useful for control of the natural user interface because any lag in the damped data results in a corresponding, or exacerbated, lag in the natural user interface display. For example, the golf swing of the avatar is jittery due to unpleasant disconnection between the raw and damped data.

The example of FIG. 3 describes a golf game. However, other types of game such as tennis, baseball, rock climbing, football also benefit from the damping logic.

Figure 4:
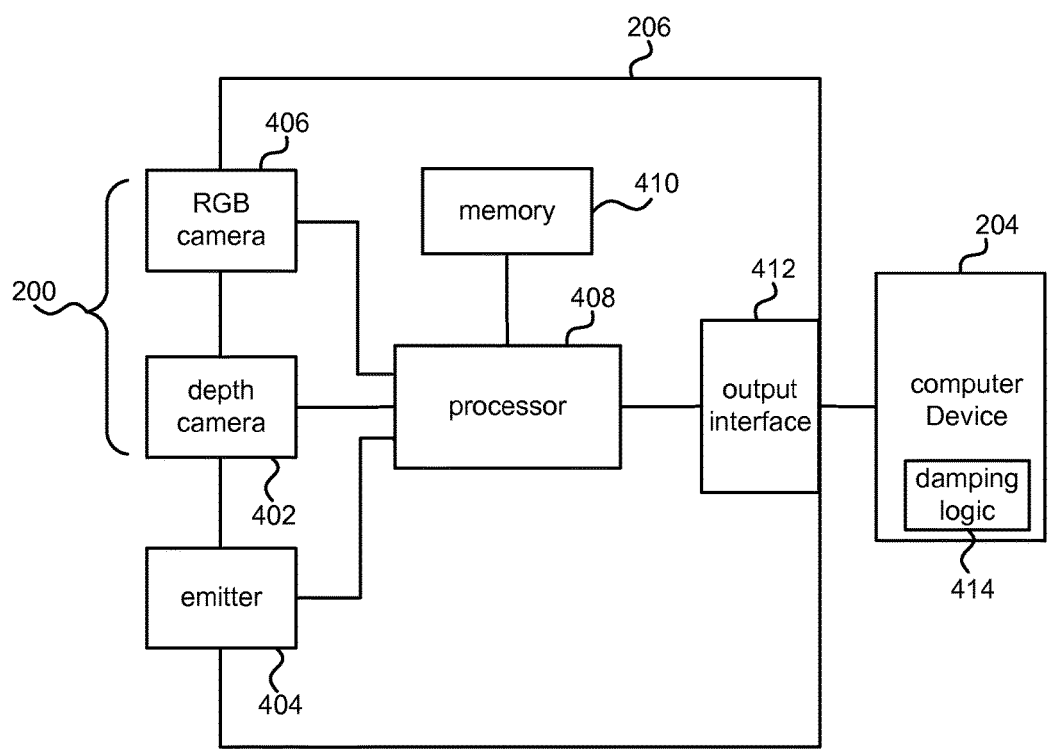
FIG. 4 is a schematic diagram of an image capture device.

FIG. 4 is a schematic diagram of the capture device 206 that can be used in the camera-based control system 200 of FIG. 2 and FIG. 3. In the examples of FIGS. 2 and 3 the capture device 206 is configured to capture video images with depth information. Such a capture device can be referred to as a depth camera. The depth information can be in the form of a depth image that includes depth values, i.e. a value associated with each image element of the depth image that is related to the distance between the depth camera and an item or object located at that image element.

The depth information can be obtained using any suitable technique including, for example, time-of-flight, structured light, stereo image, or the like. In some examples, the capture device 206 can organize the depth information into "Z layers," or layers that may be perpendicular to a Z-axis extending from the depth camera along its line of sight.

The capture device 106 comprises at least one imaging sensor 400 comprising, in this example, an RGB camera 406 and a depth camera 402 arranged to capture a depth image of a scene. The captured depth image can include a two-dimensional (2-D) area of the captured scene where each image element in the 2-D area represents a depth value such as a length or distance of an object in the captured scene from the depth camera 402.

The capture device can also include an emitter 404 arranged to illuminate the scene in such a manner that depth information can be ascertained by the depth camera 402. For example, in the case that the depth camera 402 is an infra-red (IR) time-of-flight camera, the emitter 404 emits IR light onto the scene, and the depth camera 402 is arranged to detect backscattered light from the surface of one or more targets and objects in the scene. In some examples, pulsed infrared light can be emitted from the emitter 404 such that the time between an outgoing light pulse and a corresponding incoming light pulse can be detected by the depth camera and measured and used to determine a physical distance from the capture device 206 to a position on the targets or objects in the scene. Additionally, in some examples, the phase of the outgoing light wave from the emitter 404 can be compared to the phase of the incoming light wave at the depth camera 402 to determine a phase shift. The phase shift can then be used to determine a physical distance from the capture device 206 to a position on the targets or objects. In a further example, time-of-flight analysis can be used to indirectly determine a physical distance from the capture device 206 to a position on the targets or objects by analyzing the intensity of the reflected beam of light over time via various techniques including, for example, shuttered light pulse imaging.

In another example, the capture device 206 can use structured light to capture depth information. In such a technique, patterned light (e.g., light displayed as a known pattern such as grid pattern or a stripe pattern) can be projected onto the scene using the emitter 404. Upon striking the surface of one or more targets or objects in the scene, the pattern becomes deformed. Such a deformation of the pattern can be captured by the depth camera 402 and then be analyzed to determine a physical distance from the capture device 206 to a position on the targets or objects in the scene.

In another example, the depth camera 402 can be in the form of two or more physically separated cameras that view a scene from different angles, such that visual stereo data is obtained that can be resolved to generate depth information. In this case the emitter 404 can be used to illuminate the scene or can be omitted.

In some examples, in addition to the depth camera 402, the capture device 206 can comprise a regular video camera, which is referred to as an RGB camera 406. The RGB camera 406 is arranged to capture sequences of images of the scene at visible light frequencies, and can hence provide images that can be used to augment the depth images. In alternative examples, the RGB camera 406 can be used instead of the depth camera 402.

The capture device 206 shown in FIG. 4 further comprises at least one processor 408, which is in communication with the imaging sensor 400 (i.e. depth camera 402 and RGB camera 406 in the example of FIG. 4) and the emitter 404. The processor 408 can be a general purpose microprocessor, or a specialized signal/image processor. The processor 408 is arranged to execute instructions to control the imaging sensor 400 and emitter 404 to capture depth images and/or RGB images. The processor 408 can also optionally be arranged to perform processing on these images, as outlined in more detail hereinafter.

In some examples the imaging sensor is used to provide silhouette images which are two dimensional binary images identifying foreground and background regions of the depth and/or RGB images captured by the imaging sensor. The silhouette images may be formed at the imaging sensor and/or processor 408 from the captured depth and RGB images. The silhouette images may be processed using the methods described herein to predict two dimensional joint positions. In this case the silhouette images can be thought of as depth images flattened to a fixed depth. The captured depth images may be used to predict three dimensional joint positions as described in more detail below.

The capture device 206 shown in FIG. 4 further includes a memory 410 arranged to store the instructions that for execution by the processor 408, images or frames of images captured by the depth camera 402 or RGB camera 406, or any other suitable information, images, or the like. In some examples, the memory 410 can include random access memory (RAM), read only memory (ROM), cache, Flash memory, a hard disk, or any other suitable storage component. The memory 410 can be a separate component in communication with the processor 408 or integrated into the processor 408.

The capture device 206 also comprises an output interface 412 in communication with the processor 408 and is arranged to provide data to the computing device 204 via a communication link. The communication link can be, for example, a wired connection and/or a wireless connection. In other examples, the output interface 412 can interface with one or more communication networks (such as the internet) and provide data to the computing device 204 via these networks.

The computer device 204 may comprise damping logic 414 such as damping logic 106 of FIG. 1. In other examples the damping logic 414 is implemented, at least in part, at processor 408 or using hardware logic components at capture device 206. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs).

Figure 5:
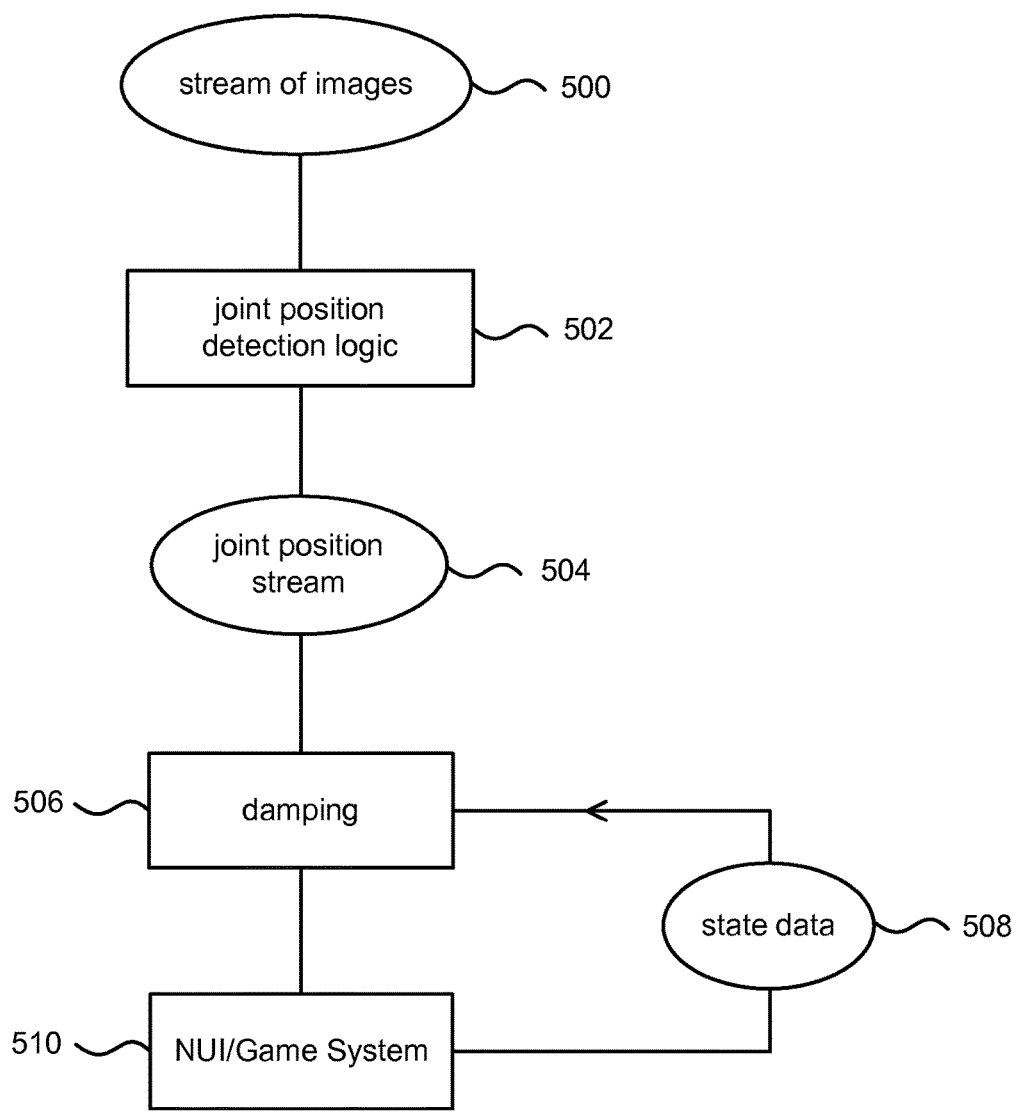
FIG. 5 is a flow diagram of a method at the camera-based control system of FIGS. 2 and 3.

FIG. 5 is a flow diagram of a method at the camera-based control system of FIGS. 2 and 3. A stream of images 500 from capture device 206 is processed by a joint position detection logic 502 to calculate positions of joints of one or more articulated entities depicted in the stream of images. The resulting joint position stream 504 is input to damping logic 506 which outputs a damped version of the joint position stream to a natural user interface or game system 510. State data 508 from the natural user interface or game system 510 may be available to the damping logic 506.

Figure 6:
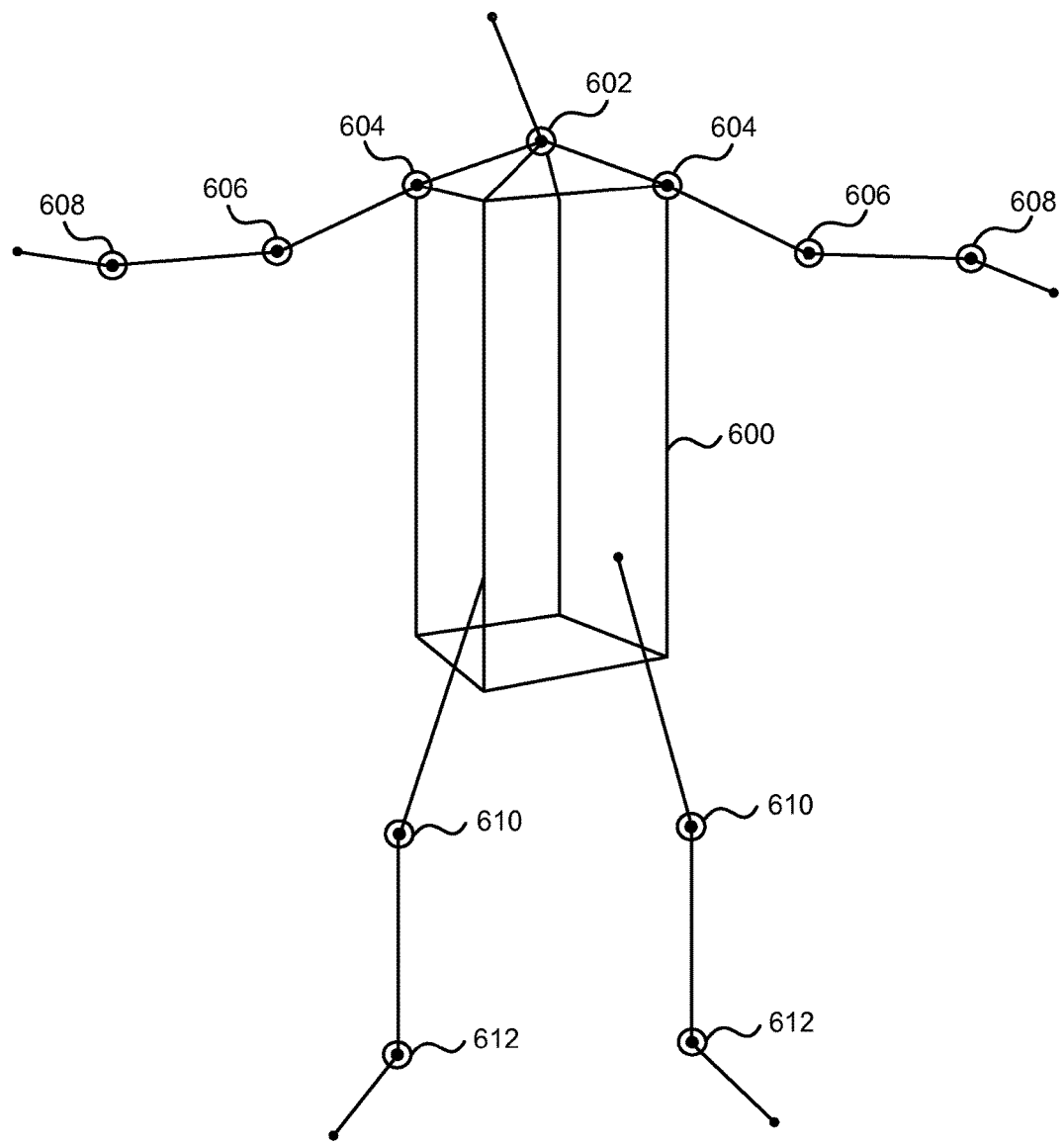
FIG. 6 is a schematic diagram of joint positions predicted in an image of a person.

The joint position detection logic 502 may be a trained machine learning system as now described. The joint position detection logic 502 may predict (from the captured image stream) joint positions of a user, for example, in the situation of FIG. 6 predicted joint positions of a user standing with his or her arms outstretched are represented schematically. In this example, predicted joint positions for the neck 602, shoulders 604, elbows 606, wrists 608, knees 610 and ankles 612 are shown. However, any number and combination of joint positions may be predicted according to the problem domain and the computing resources available. Using the joint positions a 3D model of the user may be constructed and used in control of the downstream system such as the game system or natural user interface.

In an example the joint position detection logic 502 is a trained machine learning system as now described with reference to FIG. 7.

Figure 7:
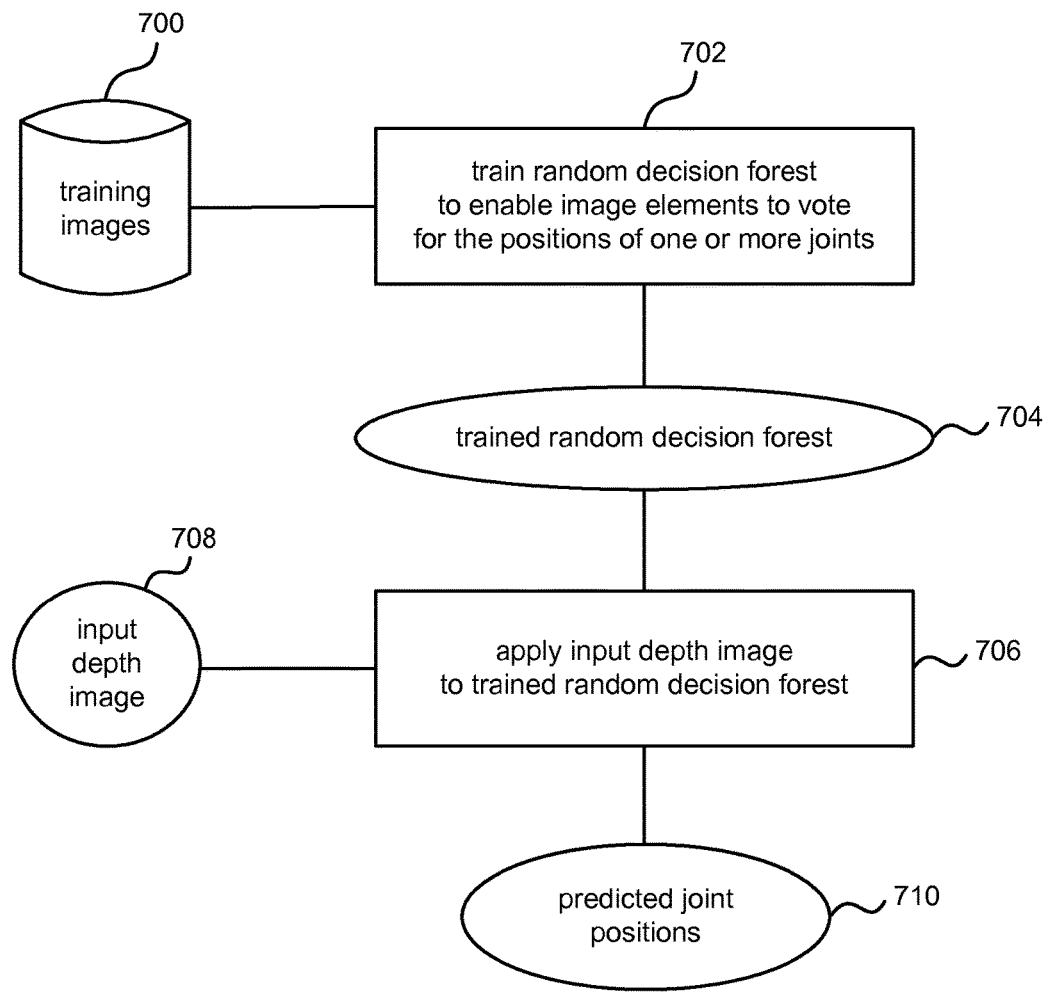
FIG. 7 is a is a flow diagram of a method of predicting joint positions in an input depth image.

FIG. 7 is a flow diagram of predicting joint positions in an input depth image 708 depicting one or more humans or animals or parts of humans or animals. A plurality of training images 700 which may be depth images that have specified joint positions is available. The images may be two dimensional, three dimensional or higher dimensional images or sequences of such images. The examples described herein use depth images but are also applicable to color images, medical images or other types of image.

A random decision forest is trained 702 to enable image elements of the training images 700 to vote for the positions of one or more joints depicted in those images. Image elements may be pixels, groups of pixels, voxels, groups of voxels, blobs, patches or other components of an image. A random decision forest comprises one or more decision trees each having a root node, a plurality of split nodes and a plurality of leaf nodes. Image elements of an image may be pushed through trees of a random decision forest from the root to a leaf node in a process whereby a decision is made at each split node. The decision is made according to characteristics of the image element and characteristics of test image elements displaced therefrom by spatial offsets specified by the parameters at the split node. At a split node the image element proceeds to the next level of the tree down a branch chosen according to the results of the decision. The random decision forest may use regression or classification. During training, parameter values (also referred to as features) are learnt for use at the split nodes and data is accumulated at the leaf nodes. For example, joint position votes are accumulated at the leaf nodes. A joint position vote is an image position (or region) where a joint is predicted to be relative to an image element making the vote. A joint position vote may be specified in any suitable manner. For example, as a vector expressing the relative distance and direction of a predicted joint position from an image element making the vote. It is not essential to use a vector, other formats may be used.

Storing all the joint position votes at the leaf nodes during training may be very memory intensive since large amounts of training data are typically used for practical applications. In some embodiments the votes are aggregated in order that they may be stored in a compact manner.

At test time a previously unseen depth image 708 is input to the system to have joint positions predicted. It is applied to the trained random decision forest 706 to obtain predicted joint positions 701. Each image element of the input depth image 708 may be sent through each tree of the trained random decision forest and joint position votes obtained from the leaves. In this way votes may be made by comparing each image element with test image elements displaced therefrom by learnt spatial offsets. Each image element may make a plurality of votes for each joint. These votes may be aggregated according to various different aggregation methods to give the predicted joint positions 710. The test time process is therefore a single stage process of applying the input depth image to the trained random decision forest to directly obtain predicted joint positions. The single stage process does not involve intermediate results such as body parts being predicted. This single stage process may be carried out in a fast and effective manner to give results in real-time and with high quality results.

The predicted joint positions 710 may be separated into individual streams, one per joint. For example, there may be a stream for the left wrist in the case of the golf game of FIG. 3. The individual streams of joint positions may be damped using damping logic 106 as now described with reference to FIG. 8.

The damping logic 106 accesses 800 a stream of data from the sensor. The stream of data has optionally been processed (for example to compute joint positions). The damping logic optionally receives 802 state data from a downstream computing system such as a game system, natural user interface, robotic system, or other system. The damping logic optionally computes 804 a velocity of the data. The velocity of the data is the change in the magnitude of the data per frame, or other element of the data stream. The damping logic 106 calculates a damped version of a data item, where the data item is a current data element of the data stream. The damped version of the data item is calculated by applying a linear or non-linear damping function to the data item. An example of a linear damping function that may be used is to calculate the damped version as being equal to the previous raw sensor data item plus a fraction of the difference between the previous raw sensor data item and the current raw sensor data item.

The damping logic 106 calculates 808 a delta between the damped version of the data item and the raw sensor data item. The raw sensor data item is referred to as "raw" because no damping has been applied to it even though the sensor data item may have been calculated from raw sensor data, such as by computing a joint position.

The damping logic 106 optionally adjusts a threshold based on one or more of: the state data received at step 802, the data velocity computed at step 804 and a counter which records frequency of use of the threshold for clamping. For example, this optional step enables the threshold to be changed on the fly. This is useful where the data being damped exhibits occasional large magnitude fast changes overlaid on lower magnitude jitter.

If the delta is found to be more than the threshold at decision point 812 the damping logic replaces the damped version by the threshold. This replacement step is referred to as clamping. Optionally the damping logic increments a counter monitoring frequency of use of the threshold for clamping.

If the delta is not more than the threshold at decision point 812 the damping logic uses 814 the damped version.

Steps 814 and 816 both proceed to input 818 the current damped data item to the system being controlled.

Figure 8:
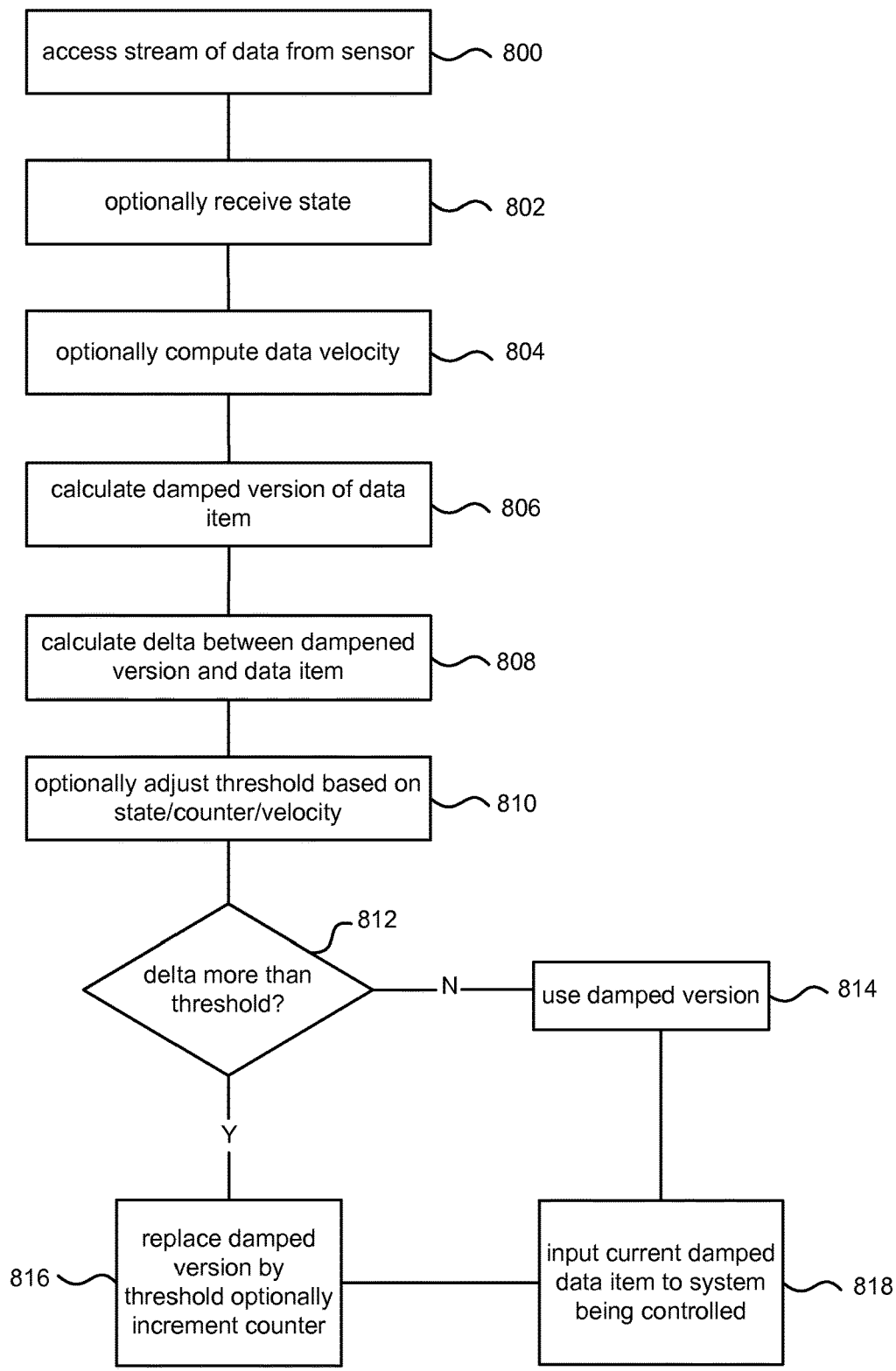
FIG. 8 is a flow diagram of a method at a damping logic.

The process of FIG. 8 may be implemented in a fast, efficient manner at the damping logic. The end result is a fast, accurate damping process with low latency that has been found particularly practical and robust in working implementations. Alternatives approaches using Kalman filters and other complex damping and/or smoothing systems are more complex, time consuming and resource intensive to compute.

When the process of FIG. 8 initializes the threshold may be set to a default value which is set according to the application domain. For example, the default value may be set by empirical testing to find a typical stationary state (of the sensor and/or an environment of the sensor) and setting the threshold to be slightly larger than background jitter observed during the stationary state.

As described above with reference to FIG. 8 the threshold may be dynamically adjusted on the basis of one or more factors. Dynamic adjustment of the threshold enables a trade-off between latency and damping to be controlled. For example, the trade-off is controlled on the basis of predicted behavior of the sensor data stream. State data may be used to make the prediction. Data velocity may also be used to make the prediction. Past threshold clamping behavior may also be used to make the prediction.

Using the one or more factors the threshold may be dynamically adjusted using a linear function or a non-linear function. Some examples are now given.

The dynamic adjustment of the threshold is particularly useful in the golf game scenario. State data from a game system indicates that a golf swing is occurring. The threshold is reduced. This results in the smoothed data following the raw data closely and reduces latency during the fast value change of the golf swing. Once the game state indicates that the golf swing has ended, or that the player is in a neutral state, the threshold is increased resulting in pleasing smooth joint positioning again.

In another example, a cursor at the user interface of FIG. 2 is controlled by the image capture system. When user interface state data indicates that the cursor is over a group of buttons (or other user interface element where small movement is anticipated), the threshold is increased to smooth noise in the sensor data. When user interface state data indicates that the cursor is over a long slider (or other user interface element where a large, fast movement is anticipated) and that the user has already gripped/selected the slider tab, the threshold may be reduced in anticipation of a long, fast movement as the control is moved, say to scroll a web page up and down.

Figure 9:
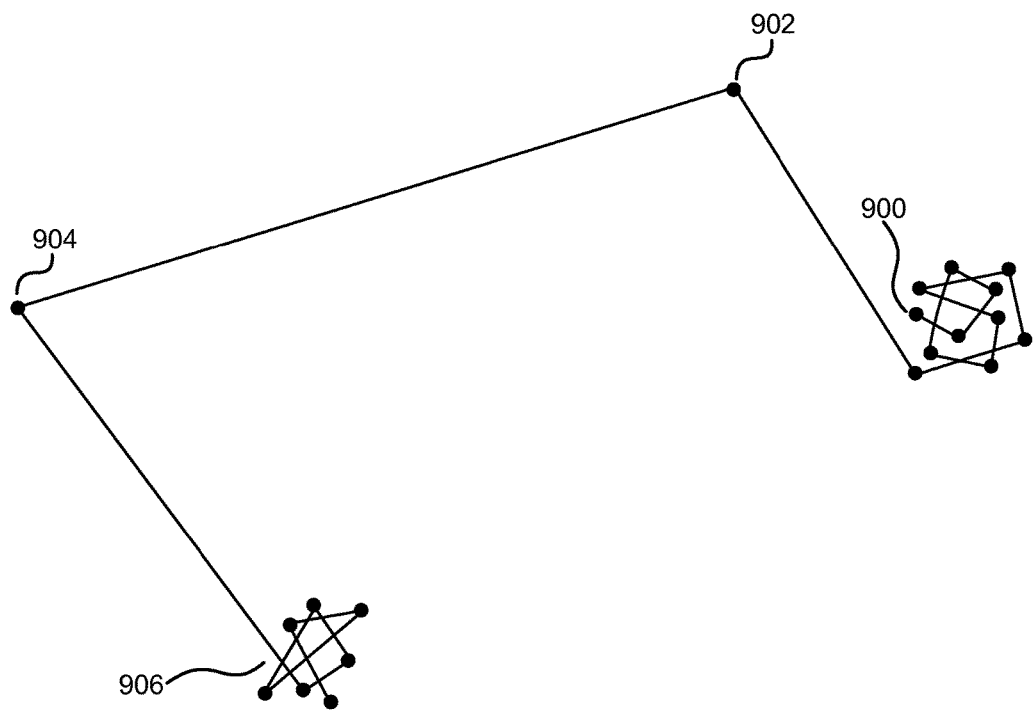
FIG. 9 is an example of a stream of 2D coordinate sensor data.

FIG. 9 shows an example of a 2D coordinate position tracking system without any damping. In this example a noisy 2D coordinate is tracked from start point 900 to end location 906. The blobs show tracked 2D coordinates and the lines between the blobs are used to indicate the sequence. The start point 900 noisily jitters giving rise to several blobs close to start point 900. The tracked 2D position then moves quickly up to point 902, then to the left at point 904 and then back down ending in a stationary but noisy position 906.

Figure 10:
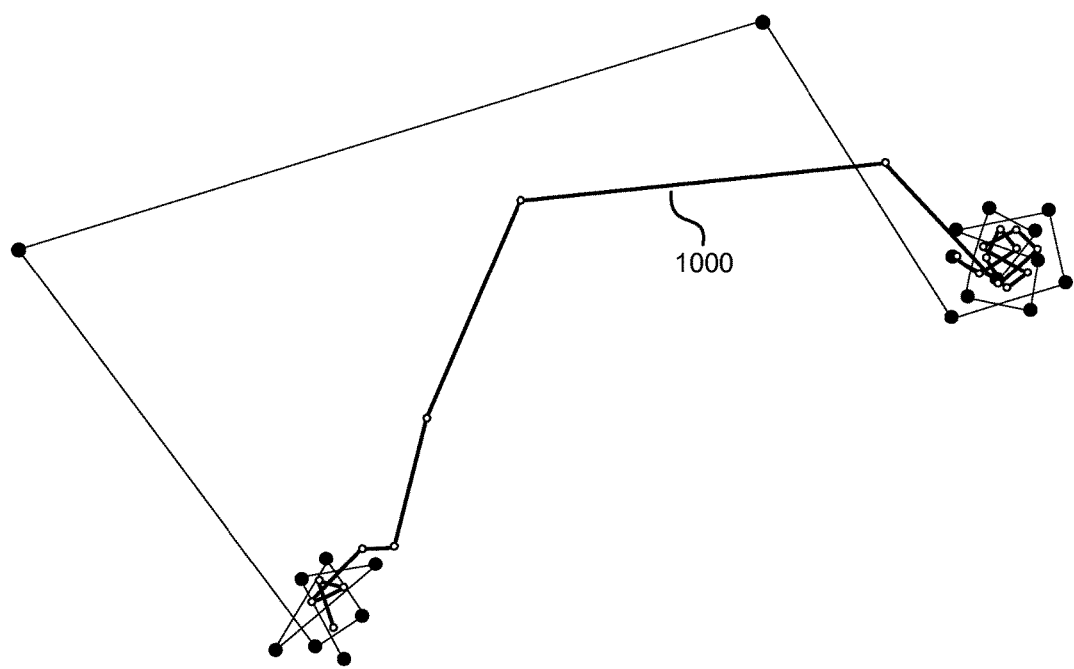
FIG. 10 is an example of the stream of 2D coordinate sensor data of FIG. 9 overlaid with a damped version of the sensor data.

FIG. 10 shows the situation of FIG. 9 with the addition of damping but without the threshold clamping of FIG. 8. The damped version of the data is shown by the points joined by thick bold line 1000. It is seen that the damping is effective locally but as soon as the data moves rapidly lag or latency is introduced. The lag or latency is shown as the difference between the shape of line 1000 and the shape of the line joining the raw data points.

Figure 11:
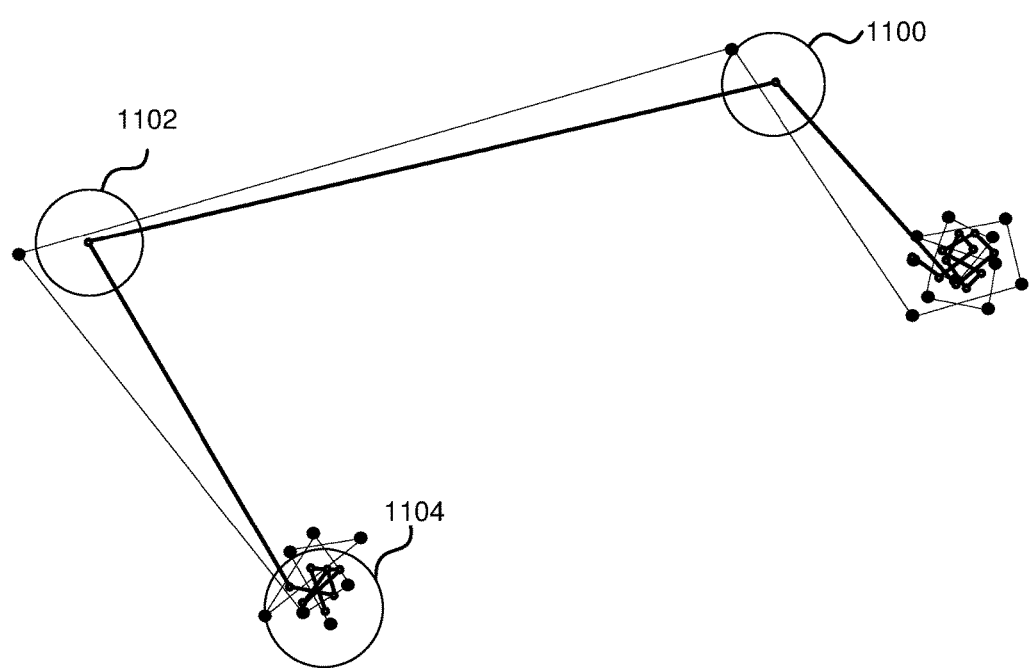
FIG. 11 is another example of the stream of 2D coordinate sensor data of FIG. 9 overlaid with a second damped version of the sensor data.

FIG. 11 shows the situation of FIG. 9 with the addition of damping combined with threshold clamping as described with reference to FIG. 8. The damped version of the data is shown by the points joined by the thick bold line. Circles 1100, 1102, 1104 show when the damped data was clamped to the threshold. The local noise is damped as in FIG. 10 but now there is significantly less latency when the position moves rapidly.

Figure 12:
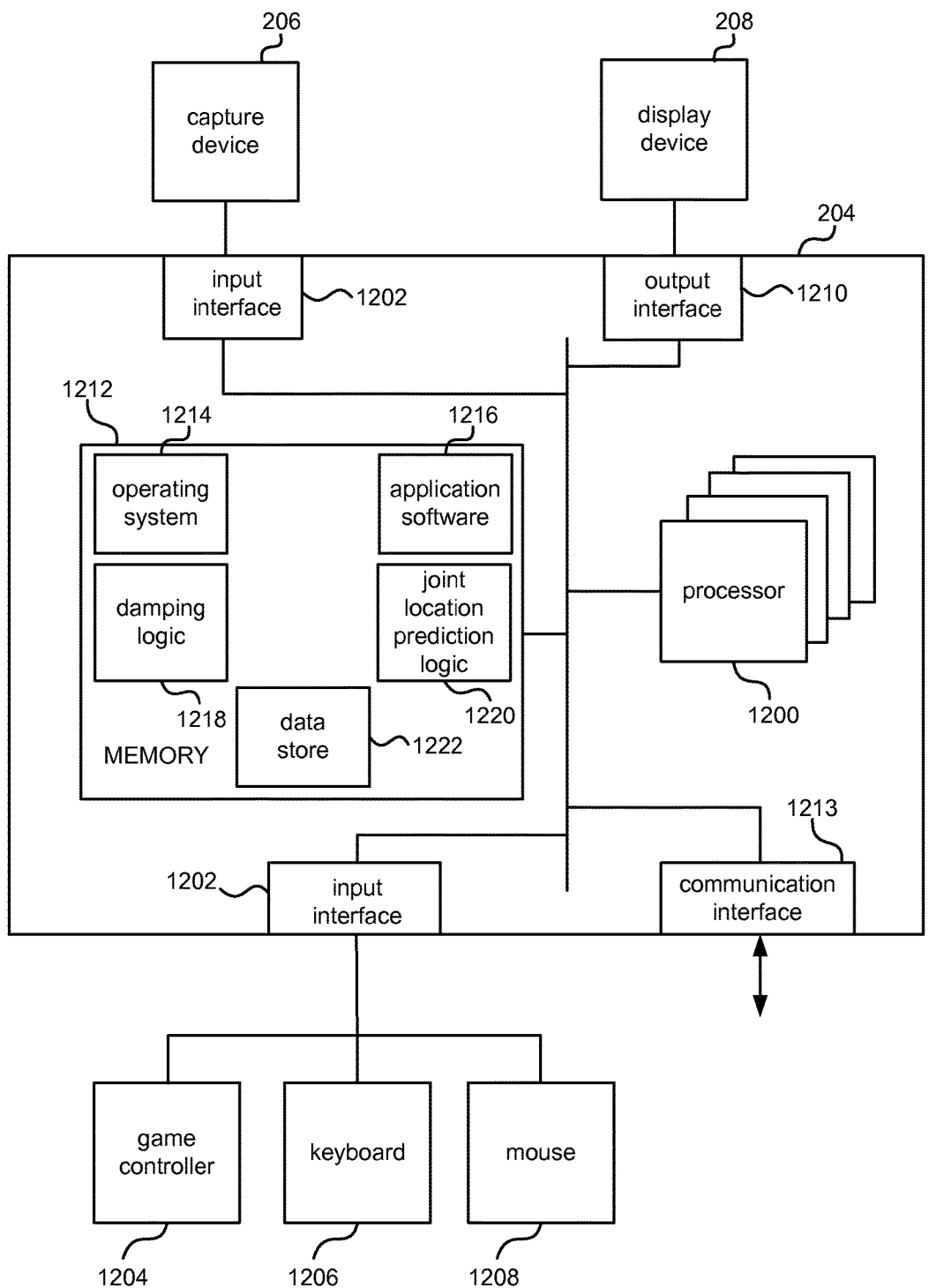
FIG. 12 illustrates an exemplary computing-based device in which embodiments of control system with a damping logic may be implemented.

FIG. 12 illustrates various components of an exemplary computing-based device 204 which may be implemented as any form of a computing and/or electronic device, and in which embodiments of sensor data damping systems may be implemented.

Computing-based device 204 comprises one or more processors 1200 which may be microprocessors, controllers, graphics processing units, parallel processing units, or any other suitable type of processors for processing computing executable instructions to control the operation of the device in order to predict joint positions in images. In some examples, for example where a system on a chip architecture is used, the processors 1200 may include one or more fixed function blocks (also referred to as accelerators) which implement a part of the method of joint positions prediction in hardware (rather than software or firmware).

The computing-based device 204 comprises one or more input interfaces 1202 arranged to receive and process input from one or more devices, such as user input devices (e.g. capture device 106, a game controller 1204, a keyboard 1206 and/or a mouse 1208). This user input may be used to control software applications, natural user interface, or games executed on the computing device 204.

The computing-based device 204 also comprises an output interface 1210 arranged to output display information to a display device 208 which can be separate from or integral to the computing device 204. The display information may provide a graphical user interface. In an example, the display device 208 may also act as the user input device if it is a touch sensitive display device. The output interface may also output data to devices other than the display device, e.g. a locally connected printing device.

The computer executable instructions may be provided using any computer-readable media that is accessible by computing based device 204. Computer-readable media may include, for example, computer storage media such as memory and communications media. Computer storage media, such as memory 1212, includes volatile and non-volatile, removable and non-removable media implemented in any method or technology for storage of information such as computer readable instructions, data structures, program modules or other data. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transport mechanism. As defined herein, computer storage media does not include communication media. Although the computer storage media (memory) is shown within the computing-based device 204 it will be appreciated that the storage may be distributed or located remotely and accessed via a network or other communication link (e.g. using communication interface 1213).

Platform software comprising an operating system 1214 or any other suitable platform software may be provided at the computing device 104 to enable application software 1216 to be executed on the device. Other software that can be executed on the computing device 104 includes: damping logic 1218 (see for example, FIG. 8 and description above); joint location prediction logic 1220 (see for example FIG. 7 and description above). A data store 1222 is provided to store data such as previously received depth images, thresholds, damped data, raw data, state data, and other data.

Any of the input interface 1202, output interface 1210, display device 208, game controller 1204, keyboard 1206, mouse 1208 and the capture device 206 may comprise NUI technology which enables a user to interact with the computing-based device in a natural manner, free from artificial constraints imposed by input devices such as mice, keyboards, remote controls and the like. Examples of NUI technology that may be provided include but are not limited to those relying on voice and/or speech recognition, touch and/or stylus recognition (touch sensitive displays), gesture recognition both on screen and adjacent to the screen, air gestures, head and eye tracking, voice and speech, vision, touch, gestures, and machine intelligence. Other examples of NUI technology that may be used include intention and goal understanding systems, motion gesture detection systems using depth cameras (such as stereoscopic camera systems, infrared camera systems, rgb camera systems and combinations of these), motion gesture detection using accelerometers/gyroscopes, facial recognition, 3D displays, head, eye and gaze tracking, immersive augmented reality and virtual reality systems and technologies for sensing brain activity using electric field sensing electrodes (EEG and related methods).

The term 'computer' or 'computing-based device' is used herein to refer to any device with processing capability such that it can execute instructions. Those skilled in the art will realize that such processing capabilities are incorporated into many different devices and therefore the terms 'computer' and 'computing-based device' each include PCs, servers, mobile telephones (including smart phones), tablet computers, set-top boxes, media players, games consoles, personal digital assistants and many other devices.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible storage media include computer storage devices comprising computer-readable media such as disks, thumb drives, memory etc. and do not include propagated signals. Propagated signals may be present in a tangible storage media, but propagated signals per se are not examples of tangible storage media. The software can be suitable for execution on a parallel processor or a serial processor such that the method steps may be carried out in any suitable order, or simultaneously.

This acknowledges that software can be a valuable, separately tradable commodity. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought.

The term 'comprising' is used herein to mean including the method blocks or elements identified, but that such blocks or elements do not comprise an exclusive list and a method or apparatus may contain additional blocks or elements.

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

The invention claimed is:

1. A computer-implemented method comprising:
    receiving a stream of sensor data from a sensor configured to capture depth data;
    damping the sensor data from the sensor configured to capture depth data to produce damped sensor data;
    determining that a difference between a current item of the stream of sensor data from the sensor configured to capture depth data and a corresponding damped item of the damped sensor data exceeds a threshold;
    on the basis of the determining, modifying the damped item by the threshold; and
    outputting the modified damped item in a stream of output data and not the damped item, thereby reducing latency in the stream of output between the damped item and the sensor data.

2. The method of claim 1, wherein the sensor data comprises features or characteristics calculated from raw sensor data.

3. The method of claim 1 wherein the sensor data is received from a capture device and comprises a stream of images.

4. The method of claim 1 comprising dynamically adjusting the threshold on the basis of state data obtained from a computing device to be controlled, at least in part, using output of the damping logic.

5. The method of claim 1 comprising dynamically adjusting the threshold on the basis of data velocity of the sensor data stream.

6. The method of claim 5 comprising calculating a data velocity of the sensor data stream.

7. The method of claim 1 comprising dynamically adjusting the threshold on the basis of past threshold clamping behavior of the damping logic with respect to the sensor data stream.

8. The method of claim 7 comprising calculating past threshold clamping behavior of the damping logic as frequency of replacing items of the damped sensor data by the threshold.

9. The method of claim 1 comprising dynamically adjusting the threshold on the basis of a combination of any two or more of: state data obtained from a computing device, data velocity of the sensor data stream, past threshold clamping behavior of the damping logic.

10. The method of claim 1 comprising setting the threshold on the basis of background jitter of the sensor data observed during a stationary state of the sensor and/or an environment of the sensor.

11. The method of claim 1 wherein the stream of sensor data comprises joint positions computed from a stream of images of an articulated entity.

12. The method of claim 1 comprising repeating the calculating and comparing steps in order to produce a stream of output data to control a computing device.

13. The method of claim 12 wherein the computing device comprises a game system.

14. The method of claim 12 wherein the computing device comprises a natural user interface.

15. A method at a damping logic comprising:
    receiving a stream of sensor data from a sensor configured to capture depth data, the sensor data comprising joint position data calculated from a stream of images;
    damping the sensor data from the sensor configured to capture depth data to produce damped sensor data;
    calculating a difference between a current item of the stream of sensor data from the sensor configured to capture depth data and a corresponding damped item from the damping logic;
    comparing the difference with a threshold;
    on the basis of the comparison, modifying the damped item by the threshold;
    replacing the damped item with the modified damped item, and thereby reducing latency in the stream of sensor data; and
    using the stream of sensor data, including the modified damped item, to control a downstream system.

16. A system comprising:
    a sensor configured to capture depth data;
    a processor;
    memory having damping logic at least partly stored in the memory and executable by the processor to:
    receive a stream of sensor data from the sensor configured to capture depth data;
    damp the sensor data from the sensor configured to capture depth data to produce damped sensor data;
    calculate a difference between a current item of the stream of sensor data from the sensor configured to capture depth data and a corresponding damped item from the damping logic;
    compare the difference with a threshold;
    on the basis of the comparison, modify the damped item by the threshold; and
    replace the damped item in a stream of output data with a modified damped item adjusted by the threshold, thereby reducing latency in the stream of output data.

17. The system of claim 16, wherein the sensor data comprises features or characteristics calculated from raw sensor data.

18. The system of claim 16, wherein the damping logic is executable by the processor to repeat the calculating and comparing steps in order to produce a stream of output data to control a computing device.

19. The system of claim 16, wherein the damping logic is executable by the processor to dynamically adjust the threshold on the basis of any one or more of: state data obtained from a computing device, data velocity of the sensor data stream, past threshold clamping behavior of the damping logic.

20. The system of claim 16, wherein the damping logic is at least partially implemented using hardware logic selected from any one or more of: a field-programmable gate array, a program-specific integrated circuit, a program-specific standard product, a system-on-a-chip, or a complex programmable logic device.

\* \* \* \* \*